US010638991B2

(12) United States Patent
Nett et al.

(10) Patent No.: US 10,638,991 B2
(45) Date of Patent: May 5, 2020

(54) SYSTEM AND METHOD FOR IMAGING A SUBJECT WITH A CONTRAST AGENT (71) Applicant: GENERAL ELECTRIC COMPANY, Schenectady, NY (US)

(72) Inventors: Brian Edward Nett, Wauwatosa, WI (US); John Howard Londt, Oconomowoc, WI (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 57 days.

(21) Appl. No.: 16/136,881

(22) Filed: Sep. 20, 2018

(65) Prior Publication Data
US 2020/0093451 A1 Mar. 26, 2020

(51) Int. Cl.
G01N 23/04 (2018.01)
A61B 6/00 (2006.01)
A61B 6/03 (2006.01)
A61B 6/02 (2006.01)

(52) U.S. Cl.
CPC .............. A61B 6/481 (2013.01); A61B 6/032 (2013.01); A61B 6/544 (2013.01); A61B 6/027 (2013.01); A61B 6/541 (2013.01)

(58) Field of Classification Search
CPC ......... A61B 6/481; A61B 6/544; A61B 6/032; A61B 6/027; A61B 6/541
See application file for complete search history.

(56) References Cited

U.S. PATENT DOCUMENTS

| 7,394,889 | B2 | 7/2008 | Partain et al. | |
| 9,042,512 | B2* | 5/2015 | Yin | A61B 6/032 250/370.09 |
| 9,928,585 | B2* | 3/2018 | Schirra | G06T 11/005 |
| 2013/0211245 | A1* | 8/2013 | Vembar | A61B 6/032 600/428 |
| 2014/0037046 | A1* | 2/2014 | Grass | A61B 6/00 378/8 |

FOREIGN PATENT DOCUMENTS

EP 2433726 A1 3/2012
WO 2015107963 A1 1/2014

* cited by examiner

Primary Examiner — Kiho Kim
(74) Attorney, Agent, or Firm — Grogan, Tuccillo & Vanderleeden, LLP (57) ABSTRACT A system for imaging a subject with a contrast agent is provided. The system includes an X-ray source, an X-ray detector, and a controller. The X-ray source is operative to transmit X-rays through the subject. The X-ray detector is operative to receive the X-rays after having passed through the subject. The controller is in electronic communication with the X-ray source and the X-ray detector and operative to: generate a target contrast level based at least in part on a contrast adjustment factor; determine when a level of the contrast agent in a first plurality of images of the subject acquired via the X-ray source and the X-ray detector reaches the target contrast level; and acquire a second plurality of images of the subject via the X-ray source and the X-ray detector after the level of the contrast agent has reached the target contrast level.

20 Claims, 5 Drawing Sheets

SYSTEM AND METHOD FOR IMAGING A SUBJECT WITH A CONTRAST AGENT

BACKGROUND

Technical Field

Embodiments of the invention relate generally to medical imaging systems, and more specifically, to a system and method for imaging a subject with a contrast agent.

Discussion of Art

In many computed tomography ("CT") imaging systems, an X-ray source/tube emits a fan-shaped X-ray beam toward a subject/object, e.g., a patient, piece of luggage or other object. The X-ray beam, after being attenuated by the subject or object, impinges upon an X-ray detector. The intensity of the attenuated X-ray radiation received at the detector is typically dependent upon the attenuation of the X-ray beam by the subject or object. Many X-ray detectors in CT imaging systems often include an array of individual detectors elements which produce separate electrical signals indicative of the attenuated X-ray radiation received by each detector element. The electrical signals are transmitted to a data processing system for analysis to ultimately produce an image. Generally, the X-ray source and the X-ray detector are rotated about the subject or object within an imaging plane via a gantry, with the imaging system obtaining a plurality of two-dimensional ("2D") projection images of the subject or object over a three-hundred-and-sixty-five degree (365°) range. After receiving the projection images, the data processing system generates a three-dimensional ("3D") image of the subject or object via tomographic image reconstruction.

Certain objects, e.g., blood vessels, are difficult to image with X-rays. As such, many CT imaging systems improve the visibility of such objects via a contrast agent, e.g., iodine, which is injected into a patient/subject prior to and/or during a scan so as to causes an object or region of interest to have a higher contrast in the generated images.

Generally, it is beneficial to reduce the amount of X-rays a patient is exposed to. It is often the case, however, that it may take some amount of time after a contrast agent is injected into the patient for the concentration of the contrast agent in the object or region of interest to be sufficient for imaging. Thus, many traditional CT imaging systems attempt to reduce a patient's X-ray exposure by anticipating when to begin "diagnostic imaging" of the object or region of interest by detecting, via "monitoring images", when a level of the contrast agent at a location in the patient downstream of the object or region of interest exceeds a pre-determined threshold. As used herein, the term "diagnostic image" refers to an image that is suitable for medical diagnostic purposes, and the term "diagnostic imaging" refers to the acquisition of diagnostic images. The term "monitoring image", as used herein, refers to an image of a subject/patient acquired by an X-ray based imaging system, at an amount of radiation exposure to the subject/patient that is lower than the typical amount of radiation exposure to the subject/patient for a diagnostic image of the subject/patient acquired by the same and/or similar X-ray based imaging system. For example, diagnostic imaging of the brain may be initiated after the level of the contrast agent in the heart has exceeded a pre-determined threshold.

The pre-determined thresholds in many traditional CT imaging systems, however, do not account for imaging factors/parameters, e.g., patient size, X-ray energy, filter settings, etc., that can affect the relationship between the detected contrast in a monitoring image and the actual level of the contrast agent at the monitored downstream location. Accordingly, traditional CT imaging systems often miscalculate when to begin diagnostic scanning in scenarios where various imaging factors deviate from the ones used to calculate the threshold. Miscalculation of when to begin diagnostic imaging, in turn, may result in deficient diagnostic images and/or increased radiation exposure to a patient.

What is needed, therefore, is an improved system and method for imaging a subject with a contrast agent.

BRIEF DESCRIPTION

In an embodiment, a system for imaging a subject with a contrast agent is provided. The system includes an X-ray source, an X-ray detector, and a controller. The X-ray source is operative to transmit X-rays through the subject. The X-ray detector is operative to receive the X-rays after having passed through the subject. The controller is in electronic communication with the X-ray source and the X-ray detector and operative to: generate a target contrast level based at least in part on a contrast adjustment factor; determine when a level of the contrast agent in a first plurality of images of the subject acquired via the X-ray source and the X-ray detector reaches the target contrast level; and acquire a second plurality of images of the subject via the X-ray source and the X-ray detector after the level of the contrast agent has reached the target contrast level.

In another embodiment, a method for imaging a subject with a contrast agent is provided. The method includes generating a target contrast level based at least in part on a contrast adjustment factor, and detecting when a level of the contrast agent in a first plurality of images of the subject has reached the target contrast level. The method further includes acquiring a second plurality of images of the subject after the level of the contrast agent has reached the target contrast level.

In yet another embodiment, another system for imaging a subject with a contrast agent is provided. The system includes an X-ray source, an X-ray detector, and a controller. The X-ray source is operative to transmit X-rays through the subject. The X-ray detector is operative to receive the X-rays after having passed through the subject. The controller is in electronic communication with the X-ray source and the X-ray detector and operative to: detect when a level of the contrast agent in a first plurality of images of the subject acquired via the X-ray source and the X-ray detector reaches a target contrast level; and acquire a second plurality of images of the subject via the X-ray source and the X-ray detector after the level of the contrast agent has reached the target contrast level. The controller determines the level of the contrast agent based at least in part from a generated material decomposition image or a simulated material decomposition image.

In still yet another embodiment, another method for imaging a subject with a contrast agent is provided. The method includes detecting when a level of the contrast agent in a first plurality of images of the subject reaches a target contrast level, and acquiring a second plurality of images of the subject after the level of the contrast agent has reached the target contrast level. The level of the contrast agent is determined based at least in part from a generated material decomposition image or a simulated material decomposition image.

DRAWINGS

The present invention will be better understood from reading the following description of non-limiting embodiments, with reference to the attached drawings, wherein below.

DETAILED DESCRIPTION

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled," "electrically connected," and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The term "real-time," as used herein, means a level of processing responsiveness that a user senses as sufficiently immediate or that enables the processor to keep up with an external process. As further used herein, the terms "imaging procedure" and/or "medical imaging procedure" refer to a medical procedure that involves an imaging system to assist in accomplishing one or more tasks such as, by way of non-limiting examples, deploying/installing a stent into a blood vessel, locating an ulcer, imaging a clogged artery, suturing a patient, and/or other medical processes.

Additionally, while the embodiments disclosed herein are described with respect to an X-ray based imaging system, e.g., a CT imaging system, it is to be understood that embodiments of the present invention are equally applicable to other devices and/or imaging systems which utilize a contrast agent to enhance image quality. Further, embodiments of the present invention related imaging systems may be used to analyze subjects within any material which can be internally imaged, generally. As such, embodiments of the present invention are not limited to analyzing subjects within human tissue.

As will be explained in greater detail below, embodiments of the present invention provide for systems and methods of imaging a subject with a contrast agent in which a scan specific/tailored target contrast level is used to determine when to begin diagnostic imaging. Additionally, embodiments of the present invention eliminate the need to account for system and/or subject properties/parameters that typically affect CT contrast imaging by providing a method for quantitively measuring the level of contrast agent in a subject via dual-energy material decomposition imaging/scanning.

Figure 1:
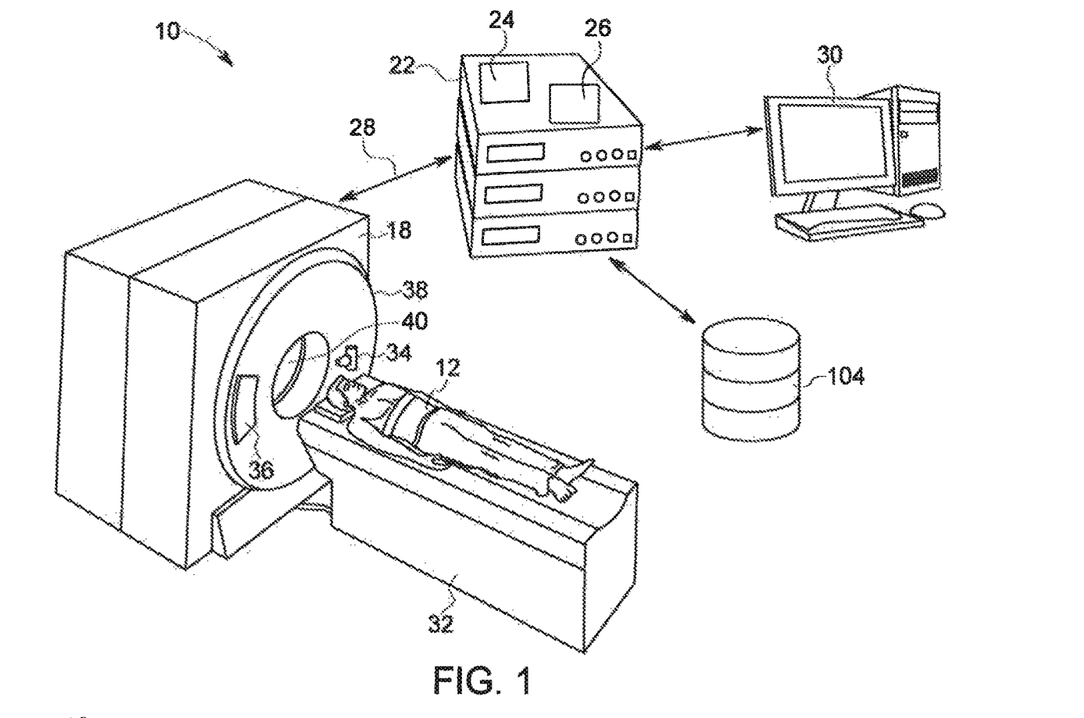
FIG. 1 is a schematic diagram of a system for imaging a subject with a contrast agent, in accordance with an embodiment of the present invention.

Accordingly, referring now to FIG. 1, the major components of a system/imaging system 10 for imaging a subject/patient 12 with a contrast agent 14 (FIG. 3), in accordance with an embodiment of the present invention, are shown. As shown in FIG. 1, the system 10 includes an assembly 18 that is utilized to scan the patient 12, and a controller 22, which includes at least one processor 24 and a memory device 26. The controller 22 may electronically communicate with the assembly 18 via one or more communication links 28 over which data generated by the assembly 18 may be passed to the controller 22. As will be appreciated, in embodiments, the imaging system 10 may further include a human-machine interface ("HMI") 30, i.e., a work station, that provides for a user/technologist/physician to interact with the imaging system 10. The imaging system 10 may further include a table 32 for supporting the patient 12 during scanning for a medical imaging procedure.

Figure 2:
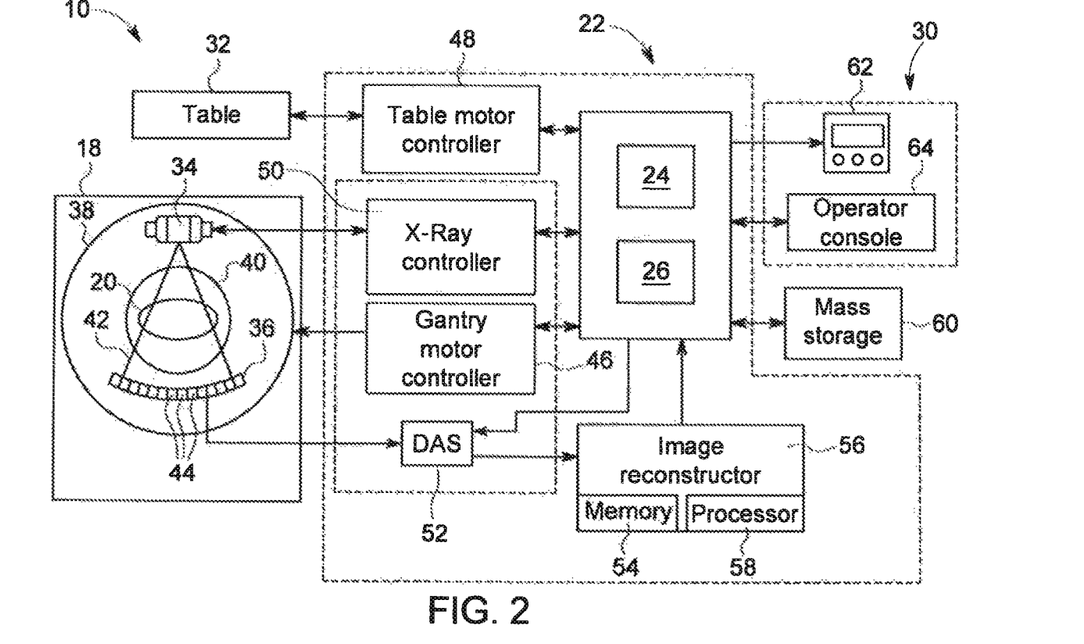
FIG. 2 is a block diagram of the system of FIG. 1, in accordance with an embodiment of the present invention.

As illustrated in FIG. 2, the assembly 18 may include an X-ray source 34 and an X-ray detector 36, which collectively form an imaging device, disposed within a rotating gantry 38 opposite one another. As will be understood, the patient 12 is positioned within a bore 40 of the gantry 38, and X-rays 42 generated/projected by the X-ray source 34 are received by the X-ray detector 36 after having passed through the patient 12 while the gantry 38 rotates about the patient 12. The X-ray detector 36 may include an array of detector elements 44, each of which produces an electric signal representative of an impinging X-ray 42 beam. While the X-rays 42 generated by the X-ray source 34 are disclosed herein as being X-rays, it will be understood that, in embodiments, the X-rays 42 may be other types of electromagnetic rays/waves, e.g., gamma rays, infrared waves, radio waves, etc.

The controller 22 may include a gantry motor controller 46, a table motor controller 48, a ray controller 50, and a data acquisition system ("DAS") 52. The table motor controller 48 governs actuation of a motor that moves the table 32 in relation to the assembly 18, the gantry motor controller 46 controls the rotational direction and/or speed of the gantry 38, the ray controller 50 provides power and timing signals to the X-ray source 34, and the DAS 52 samples analog projection data from the detector elements 44 and converts the analog data to digital projection data for subsequent processing. For example, in embodiments, the digital projection data may be loaded from the DAS 52 into a memory 54 device of an image reconstructor 56 where it is used by a processor 58 to reconstruct one or more images via an image reconstruction algorithm. The one or more images may then be sent to the HMI 30 and/or a mass storage device 60, e.g., a large computerized data storage apparatus such as a network attached storage ("NAS") device.

The HMI 30 includes a monitor 62 for displaying the reconstructed images, and a console 64, e.g., buttons, dials, a touch screen, a keyboard, and/or a mouse, for receiving command/scanning parameters from an operator of the system 10.

Figure 3:
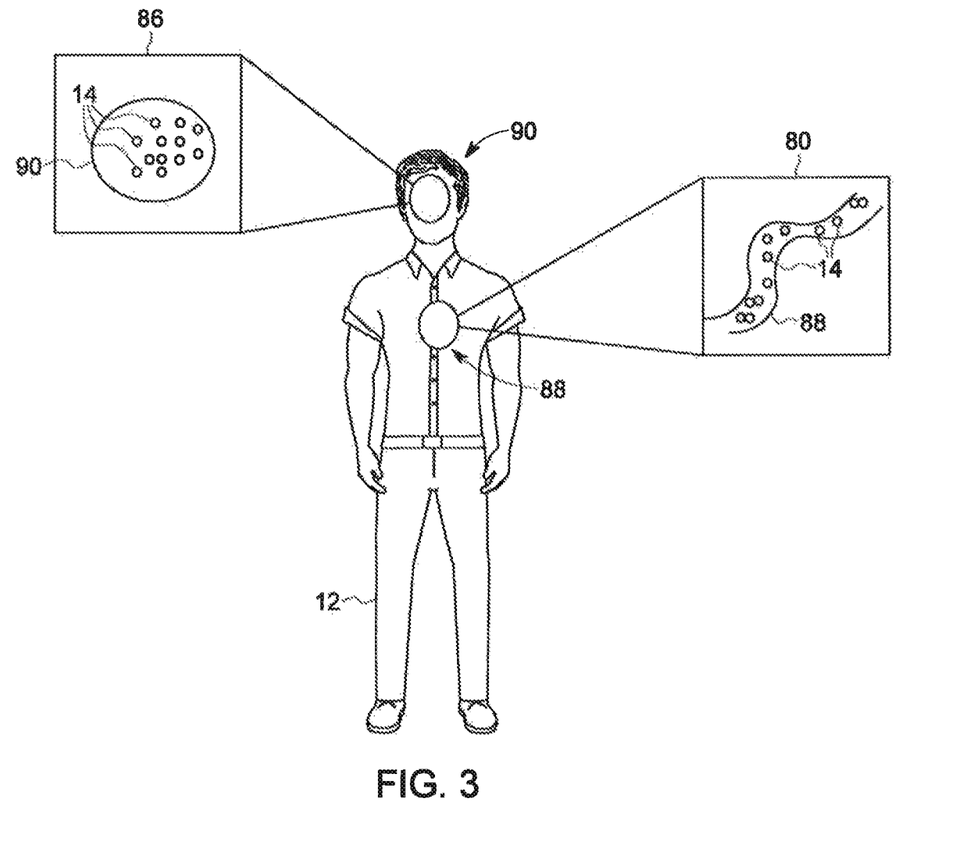
FIG. 3 is a diagram of a monitoring site and a diagnostic site of the subject of FIG. 1, in accordance with an embodiment of the present invention.
Figure 4:
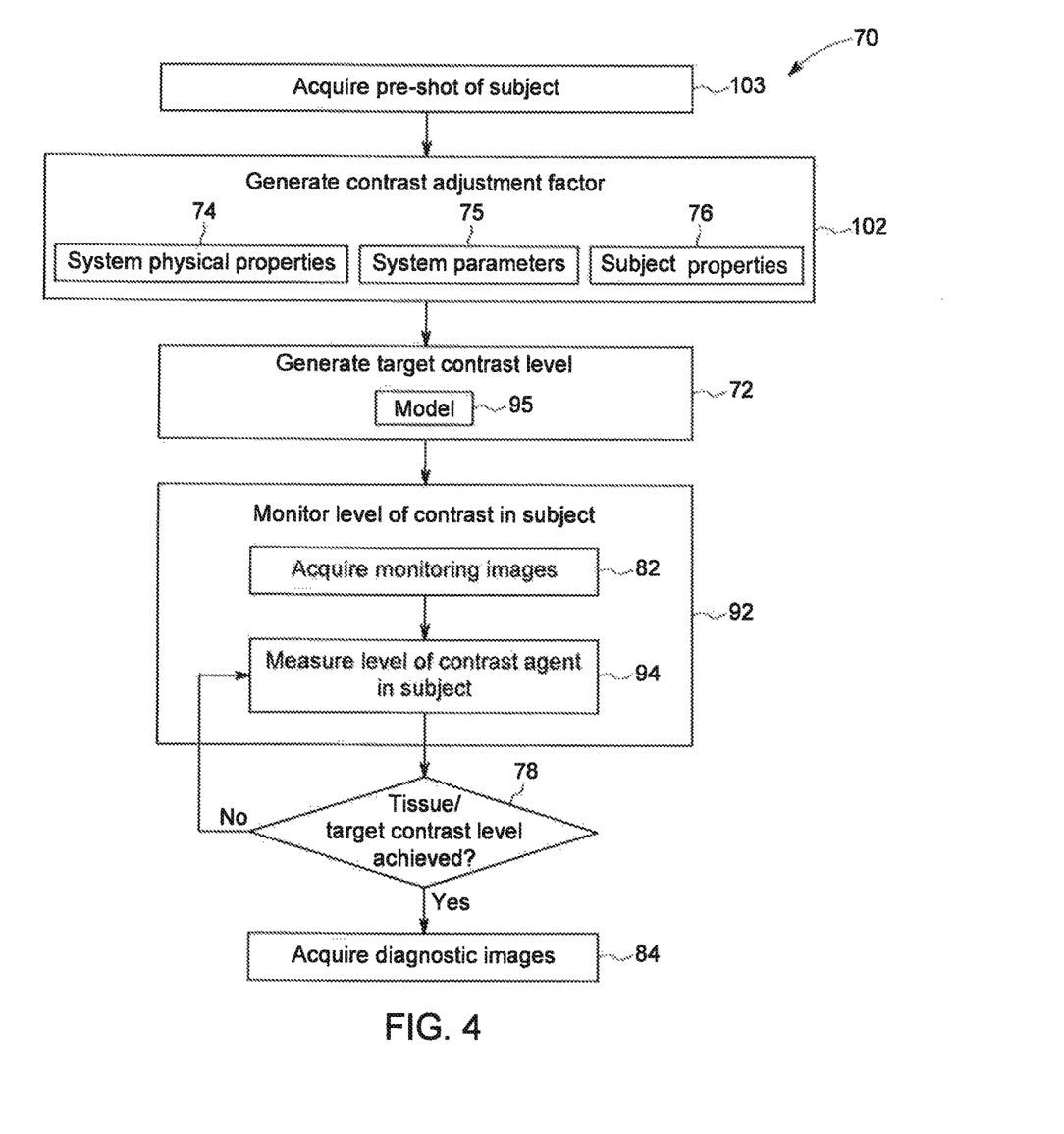
FIG. 4 is a flow chart depicting a method of imaging the subject with a contrast agent utilizing the system of FIG. 1, in accordance with an embodiment of the present invention.

Turning now to FIGS. 3 and 4, a method 70 for imaging the patient/subject 12 utilizing the system 10 (FIG. 1), in accordance with an embodiment of the present invention, is shown. The method 70 includes generating 72 a target contrast level, e.g., a threshold, based at least in part on a contrast adjustment factor 74, 75, 76; detecting 78 when a level of the contrast agent 14 (FIG. 3) in a first plurality of images 80, acquired 82 by the system 10, of the patient 12 has reached, e.g., is greater than or equal to, the target contrast level; and acquiring 84 a second plurality of images 86 of the patient 12 after the level of the contrast agent 14 has reached the target contrast level. As used herein, the term "contrast adjustment factor" refers to a parameter/factor/property that affects the relationship between the detected level of contrast agent at a monitoring site and the actual level of the contrast agent at the monitoring site.

For example, as shown in FIG. 3, in embodiments, the first plurality of images 80 may be monitoring images that depict/track the level of the contrast agent 14 as a first location/monitoring site/region of interest 88, e.g., a blood vessel in the heart of the patient 12. Upon detecting 78 that the contrast agent 14 at the monitoring site 88 has reached the target contrast level, the system 10 may then proceed to diagnostic imaging 84 of a second location/target site/region of interest 90, e.g., tissue and/or blood vessels in the brain of the patient 12.

As further shown in FIG. 4, in embodiments, acquisition 82 of the monitoring images 80 and/or detection 78 of the contrast level reaching the target contrast level may take place within an encompassing monitoring process 92 that may additionally include determining/measuring 94 the level of the contrast agent 14 at the monitoring site 88. As will be appreciated, the controller 22 (FIG. 1) may determine/measure 94 the level of the contrast agent 14 at the monitoring site 88 based at least in part on the contrast, e.g., the HU/CT number, of the pixels of the monitoring images 80. For example, in embodiments, detection 78 may be based at least in part on determining if the contrast adjustment factor multiplied by the measured 94 contrast agent 14 is greater than the target contrast level, e.g., a threshold. As will be understood, however, other embodiments may employ other suitable threshold/triggering algorithms such as predictive algorithms that incorporate historical data. Embodiments may also include a plurality of target contrast levels each corresponding to a different monitoring region of the subject 12. In embodiments, determining 78 whether to proceed to diagnostic acquisition 84 may be based on taking the average of the measured 94 contrast agent at two different monitoring locations of the subject 12.

As will be understood, in embodiments, the contrast adjustment factor may be based at least in part on the patient 12 and/or the X-ray source 34 (FIG. 1). For example, the contrast adjustment factor may be: a system physical property 74, e.g., a physical property of the system 10 such as the type of filter through which the X-rays 42 pass; a system parameter 75, e.g., a variable property of the system 10 such as an energy potential setting of the X-ray source 34, i.e., the kVp between the anode and cathode of the X-ray source 34; a subject property 76, e.g., a property and/or factor of the subject such as a size of the patient 12, a density of the patient 12 and/or other characteristics of the patient 12; and/or other suitable factors and parameters/properties.

In embodiments, the system 10 may generate/estimate 102 the contrast adjustment factor 74, 75 and/or 76 via a pre-shot/scout image 103, operator input via the HMI 30 (FIG. 2), and/or retrieval from a database 104 (FIG. 1). As used herein, the terms "pre-shot" and "scout image" refer to an image acquisition taken of the subject 12, often at radiation exposure levels lower than those at which the diagnostic images 86 are acquired 84, acquired 103 prior to acquisition 82 of the monitoring images 80.

Figure 5:
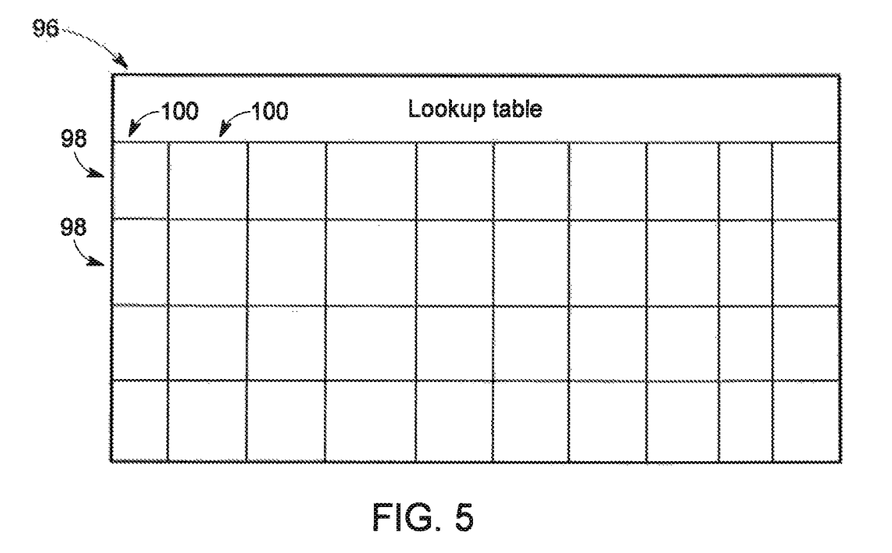
FIG. 5 is a diagram of a lookup table of the method if FIG. 4, in accordance with an embodiment of the present invention.
Figure 6:
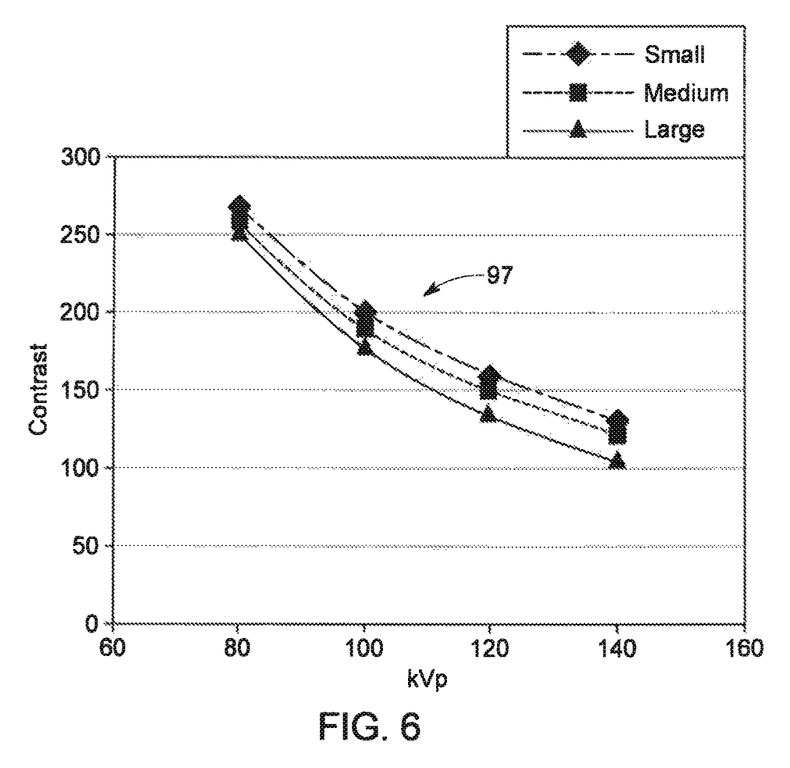
FIG. 6 is a graph plotting contrast agent level against X-ray source potential, in accordance with an embodiment of the present invention.

As yet further shown in FIG. 4, in embodiments, generation 72 of the target contrast level may be based at least in part on a contrast model 95. For example, in embodiments, the contrast model 95 may include/be based at least in part on a look-up table 96 (FIG. 5) having a data structure, e.g., rows 98 and columns 100, that correlate one or more contrast adjustment factors 74, 75, 76 to known levels of the contrast agent 14. For example, in embodiments, the lookup table 96 may include information capturing the curves 97 shown in FIG. 6, depicting the trend of lower X-ray source energy potentials resulting in higher contrast of the contrast agent 14. While FIG. 5 depicts the contrast model 95 as including a lookup table 96, it will be understood that the contrast model 95 may take other forms.

In embodiments, an operator of the system 10 may set a desired contrast enhancement level in HU for a given/reference X-ray source 34 potential in order to maintain a desired contrast to noise ratio ("CNR") in the diagnostic images 86. Further, in embodiments, the controller 22 may automatically adjust the window width to window level ("WW/WL") ratio based at least in part on the desired X-ray source potential and the measured 94 level of the contrast agent 14, which as will be appreciated, may provide for a more consistent look and/or feel of the final 3D image.

Figure 7:
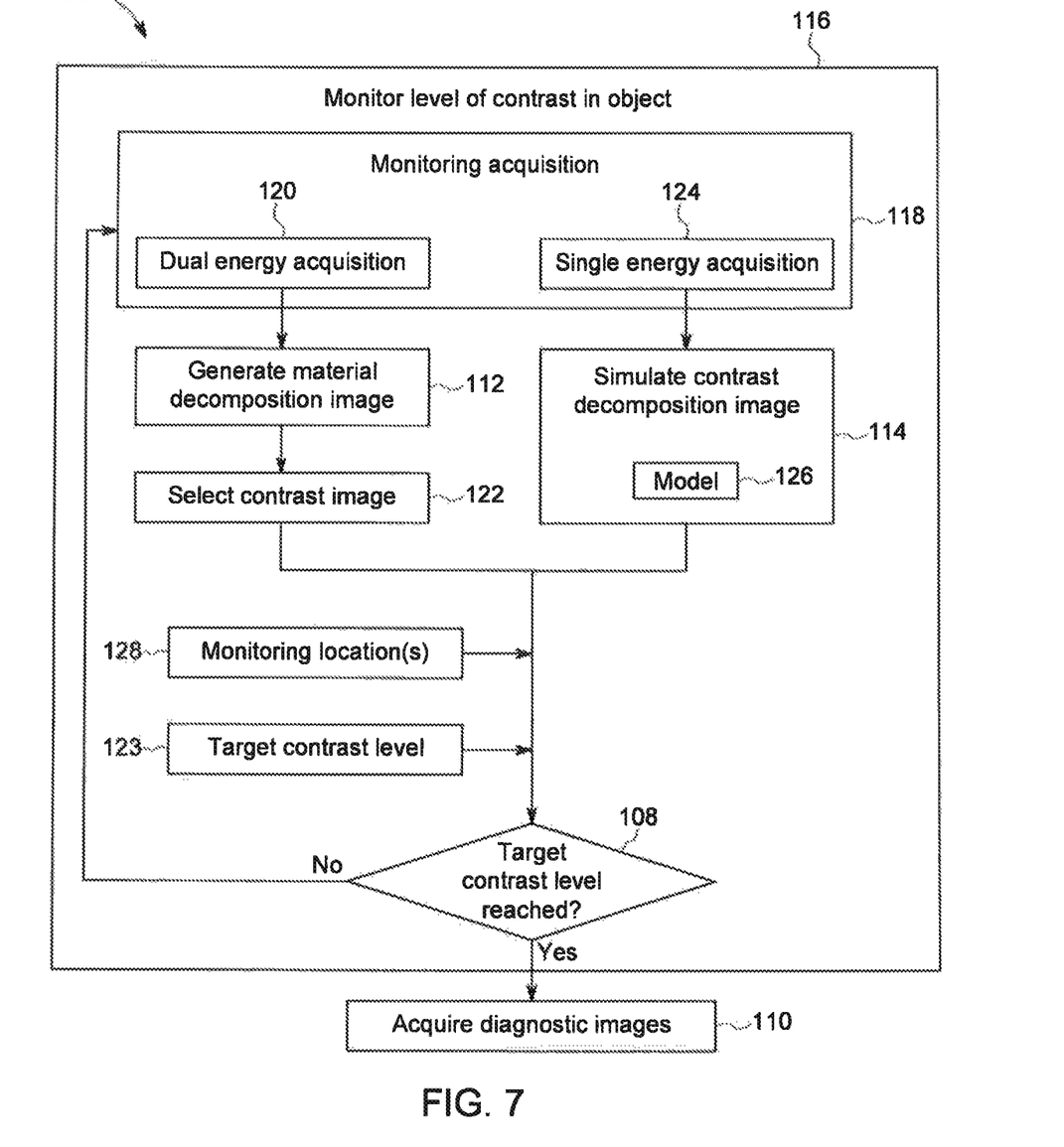
FIG. 7 is flow chart depicting another method of imaging the subject with a contrast agent utilizing the system of FIG. 1, in accordance with an embodiment of the present invention.

Referring now to FIGS. 3 and 7, in embodiments, the system 10 (FIG. 1) may generate/begin acquisition of the monitoring images based at least in part on an indirect quantitative assessment of the contrast agent in the monitoring images. In such embodiments, the target contrast level may be entered, e.g., via HMI 30, or generated in accordance with the method 70 (FIG. 4) discussed above. Accordingly, another method 106 (FIG. 7) for imaging the patient 12 with the contrast agent 14 utilizing the system 10 (FIG. 1), in accordance with an embodiment of the present invention, is shown. Similar to the method 70 shown in FIG. 4, the method 106 includes detecting 108 when a level of the contrast agent 14 in a first plurality of images 80 of the subject 12 reaches a target contrast level; and acquiring 110 a second plurality of images 86 of the subject 12 after the level of the contrast agent 14 has reached the target contrast level. As stated above, however, the level of the contrast agent 14 is determined based at least in part on a generated 112 material decomposition image, e.g., an image generated from the acquisition of two or more images of the contrast agent 14 in the subject 12 wherein at least two of the images are acquired at different X-ray source energy potentials/levels; and/or a simulated 114 material decomposition image.

For example, in embodiments, the system 10 may monitor 116 the level of the contrast agent 14 in the subject 12 by acquiring 118 monitoring images 80 via dual energy acquisition 120 or other suitable energy discriminating acquisition such as a photon acquisition detection/counting. The system 10 may then generate 112 the material decomposition image from the acquired 118 dual-energy monitoring images 120. As will be understood, in embodiments, the level of the contrast agent 14 may then be determined via the controller 22 from a contrast image 122, e.g., a type of material decomposition image based at least in part on the generated 112 material decomposition image. The level of the contrast agent 14 in the contrast image 122 may then be compared 108 to a target contrast level. In embodiments, the target contrast level may be entered 123 into the system via the HMI 30 and/or determined in a manner akin to the method 70 (FIG. 4) discussed above.

As also shown in FIG. 7, in embodiments, the system 10 may acquire 118 the monitoring images 80 via a single energy acquisition 124, and then simulate 114 a material decomposition image from the single energy acquisition 124. In embodiments, simulation 114 of the material decomposition image may be based at least in part on a model 126, e.g., a convolutional neural network or other suitable artificial intelligence algorithm. In embodiments, the contrast model 126 may be a contrast agent mapping, e.g., an iodine map derived from the single acquisition 124 monitoring images 80. The contrast agent mapping may display units, e.g., mg/cc, of the contrast agent 14 and/or show values of X-ray source potential, e.g., kVp. In other words, in embodiments, determination 108 whether to proceed to diagnostic acquisition 110 may be based on comparing a simulated 114 material decomposition image to a pre-determined/desired target contrast threshold 123.

Further, in embodiments, the determination/detection 108 of whether the level of contrast in the monitoring images 80 has reached the target contrast level may be based at least in part on one or more monitoring locations 128, i.e., the locations of the patient 12 from which the monitoring images 80 are acquired from, e.g., the heart, the abdomen, the leg, etc.

Finally, it is also to be understood that the imaging system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein, which may be accomplished in real-time. For example, as previously mentioned, the system may include at least one processor and system memory/data storage structures, which may include random access memory (RAM) and read-only memory (ROM). The at least one processor of the system may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium," as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a system for imaging a subject with a contrast agent is provided. The system includes an X-ray source, an X-ray detector, and a controller. The X-ray source is operative to transmit X-rays through the subject. The X-ray detector is operative to receive the X-rays after having passed through the subject. The controller is in electronic communication with the X-ray source and the X-ray detector and operative to: generate a target contrast level based at least in part on a contrast adjustment factor; determine when a level of the contrast agent in a first plurality of images of the subject acquired via the X-ray source and the X-ray detector reaches the target contrast level; and acquire a second plurality of images of the subject via the X-ray source and the X-ray detector after the level of the contrast agent has reached the target contrast level. In certain embodiments, the contrast adjustment factor is based at least in part on at least one of: a physical property of the system; a parameter of the system; and a property of the subject. In certain embodiments, the contrast adjustment factor is based at least in part on one of: a size of the subject; and an energy potential setting of the X-ray source. In certain embodiments, the first plurality of images are monitoring images and the second plurality of images are diagnostic images. In certain embodiments, the target contrast level is based at least in part on a contrast model. In certain embodiments, the contrast model is based at least in part on a lookup table. In certain embodiments, the contrast model is based at least in part on a machine learning algorithm. In certain embodiments, the target contrast level is based at least in part on a material decomposition image. In certain embodiments, the contrast adjustment factor is based at least in part on a scout image of the subject.

Other embodiments provide for a method for imaging a subject with a contrast agent. The method includes generating a target contrast level based at least in part on a contrast adjustment factor, and detecting when a level of the contrast agent in a first plurality of images of the subject has reached the target contrast level. The method further includes acquiring a second plurality of images of the subject after the level of the contrast agent has reached the target contrast level. In certain embodiments, the contrast adjustment factor is based at least in part on one of: a physical property of the system; a parameter of the system; and a property of the subject. In certain embodiments, the contrast adjustment factor is based at least in part on at least one of: a size of the subject; and an energy potential setting of an X-ray source. In certain embodiments, the first plurality of images are monitoring images and the second plurality of images are diagnostic images. In certain embodiments, the target contrast level is based at least in part on a material decomposition image.

Yet still other embodiments provide for another system for imaging a subject with a contrast agent. The system includes an X-ray source, an X-ray detector, and a controller. The X-ray source is operative to transmit X-rays through the subject. The X-ray detector is operative to receive the X-rays after having passed through the subject. The controller is in electronic communication with the X-ray source and the X-ray detector and operative to: detect when a level of the contrast agent in a first plurality of images of the subject acquired via the X-ray source and the X-ray detector reaches a target contrast level; and acquire a second plurality of images of the subject via the X-ray source and the X-ray detector after the level of the contrast agent has reached the target contrast level. The controller determines the level of the contrast agent based at least in part from a generated material decomposition image or a simulated material decomposition image. In certain embodiments, the first plurality of images are monitoring images acquired vial dual-energy scanning and the second plurality of images are diagnostic images. In certain embodiments, the generated material decomposition image is based at least in part on the monitoring images. In certain embodiments, the controller is further operative to: acquire the first plurality of images via single energy scanning; and generate the simulated material decomposition image by simulating a dual energy scanning of the first plurality of images.

Yet still other embodiments provide for another method for imaging a subject with a contrast agent. The method includes detecting when a level of the contrast agent in a first plurality of images of the subject reaches a target contrast level, and acquiring a second plurality of images of the subject after the level of the contrast agent has reached the target contrast level. The level of the contrast agent is determined based at least in part from a generated material decomposition image or a simulated material decomposition image. In certain embodiments, the first plurality of images are monitoring images acquired via dual-energy scanning, and the second plurality of images are diagnostic images. In certain embodiments, the generated decomposition image is based at least in part on the monitoring images.

Accordingly, as will be appreciated, by using a target contrast level that is based at least in part on contrast adjustment factors corresponding to a specific scan of a subject, as opposed to using the same pre-determined threshold for every scan, some embodiments of the present invention provide for improved anticipation/calculation of when to begin diagnostic imaging/scanning of the subject over traditional contrast imaging systems/methods. Thus, some embodiments of the present invention provide for reduced X-ray radiation exposure to a patient as compared to traditional CT imaging systems/methods.

Further, by generating a target contrast level based on scan specific contrast adjustment factors, some embodiments of the present invention provide for the ability to use lower X-ray source potentials, e.g., less than one-hundred-and-twenty (120) kVp, which in turn, reduces the amount of X-ray radiation exposure to a patient and/or the amount of contrast agent injected into the patient, as compared to traditional CT imaging systems.

Further still, by providing for a tailored target contrast level, some embodiments of the present invention may provide for a reduction in the number of views/projections per rotation, of a CT imaging system, such that the energy separation in a dual energy imaging/scanning procedure is higher than traditional fast switching acquisitions.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their subjects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A system for imaging a subject with a contrast agent, the system comprising:
    an X-ray source operative to transmit X-rays through the subject;
    an X-ray detector operative to receive the radiation rays after having passed through the subject; and
    a controller in electronic communication with the X-ray source and the X-ray detector and operative to:
        generate a target contrast level based at least in part on a contrast adjustment factor;
        determine when a level of the contrast agent in a first plurality of images of the subject acquired via the X-ray source and the X-ray detector reaches the target contrast level; and acquire a second plurality of images of the subject via the X-ray source and the X-ray detector after the level of the contrast agent has reached the target contrast level.

2. The system of claim 1, wherein the contrast adjustment factor is based at least in part on at least one of:
a physical property of the system;
a parameter of the system; and
a property of the subject.

3. The system of claim 2, wherein the contrast adjustment factor is based at least in part on one of:
a size of the subject; and
an energy potential setting of the X-ray source.

4. The system of claim 1, wherein the first plurality of images are monitoring images and the second plurality of images are diagnostic images.

5. The system of claim 1, wherein the target contrast level is based at least in part on a contrast model.

6. The system of claim 5, wherein the contrast model is based at least in part on a lookup table.

7. The system of claim 1, wherein the contrast adjustment factor is based at least in part on a scout image of the subject.

8. The system of claim 1, wherein the target contrast level is based at least in part on a material decomposition image.

9. A method for imaging a subject with a contrast agent, the method comprising:
generating a target contrast level based at least in part on a contrast adjustment factor;
detecting when a level of the contrast agent in a first plurality of images of the subject has reached the target contrast level; and
acquiring a second plurality of images of the subject after the level of the contrast agent has reached the target contrast level.

10. The method of claim 9, wherein the contrast adjustment factor is based at least in part on one of:
a physical property of the system;
a parameter of the system; and
a property of the subject.

11. The method of claim 10, wherein the contrast adjustment factor is based at least in part on at least one of:
a size of the subject; and
an energy potential setting of an X-ray source.

12. The method of claim 9, wherein the first plurality of images are monitoring images and the second plurality of images are diagnostic images.

13. The method of claim 9, wherein the target contrast level is based at least in part on a material decomposition image.

14. A system for imaging a subject with a contrast agent, the system comprising:
an X-ray source operative to transmit X-rays through the subject;
an X-ray detector operative to receive the X-rays after having passed through the subject;
a controller in electronic communication with the X-ray source and the X-ray detector and operative to:
detect when a level of the contrast agent in a first plurality of images of the subject acquired via the X-ray source and the X-ray detector reaches a target contrast level; and
acquire a second plurality of images of the subject via the X-ray source and the X-ray detector after the level of the contrast agent has reached the target contrast level; and
wherein the controller determines the level of the contrast agent based at least in part from a generated material decomposition image or a simulated material decomposition image.

15. The system of claim 14, wherein the first plurality of images are monitoring images acquired vial dual-energy scanning and the second plurality of images are diagnostic images.

16. The system of claim 15, wherein the generated material decomposition image is based at least in part on the monitoring images.

17. The system of claim 14, wherein the controller is further operative to:
acquire the first plurality of images via single energy scanning; and
generate the simulated material decomposition image by simulating a dual energy scanning of the first plurality of images.

18. A method for imaging a subject with a contrast agent, the method comprising:
detecting when a level of the contrast agent in a first plurality of images of the subject reaches a target contrast level;
acquiring a second plurality of images of the subject after the level of the contrast agent has reached the target contrast level; and
wherein the level of the contrast agent is determined based at least in part from a generated material decomposition image or a simulated material decomposition image.

19. The method of claim 18, wherein the first plurality of images are monitoring images acquired via dual-energy scanning, and the second plurality of images are diagnostic images.

20. The method of claim 19, wherein the generated decomposition image is based at least in part on the monitoring images.

* * * * *